United States Patent

Iijima

[11] Patent Number: 5,910,833
[45] Date of Patent: Jun. 8, 1999

[54] OPHTHALMIC INSTRUMENT

[75] Inventor: Hiroshi Iijima, Tokyo, Japan

[73] Assignee: Kabushiki Kaisha TOPCON, Tokyo, Japan

[21] Appl. No.: 09/093,607

[22] Filed: Jun. 9, 1998

[30] Foreign Application Priority Data

Jun. 11, 1997 [JP] Japan ................................. 9-153594

[51] Int. Cl.⁶ ........................................................ A61B 3/00
[52] U.S. Cl. ........................................................ 351/208
[58] Field of Search ................................... 351/105, 208, 351/209, 211, 221; 606/5, 4, 10, 13

[56] References Cited

U.S. PATENT DOCUMENTS 5,098,426 3/1992 Sklar et al. ............................. 351/209
5,258,791 11/1993 Penney et al. ........................ 351/211
5,532,769 7/1996 Miwa et al. ............................ 351/105

FOREIGN PATENT DOCUMENTS

8-266475 10/1996 Japan .

Primary Examiner—George Manuel
Attorney, Agent, or Firm—Finnegan, Henderson, Farabow, Garrett & Dunner, L.L.P.

[57] ABSTRACT

A stopper knob (108) is provided on the side surface of a base (101). If a joy stick (107) is tilted forward lowering the stopper knob (108), a platform frame (109) advances, and the main body of an instrument can be roughly aligned with a subject eye to be tested. If the alignment is completed, the stopper knob (108) is released. In the ophthalmic instrument of the present invention, automatic alignment which performs precise alignment on the subject eye is not started by only releasing the stopper knob (108). The ophthalmic instrument is provided with a microswitch (111). When the platform frame (109) is pulled on a tester's side by the joy stick (operating stick) (107) and the microswitch (111) engages with a protruding portion (112) fixed to the base (101), automatic alignment is started.

3 Claims, 9 Drawing Sheets

OPHTHALMIC INSTRUMENT

BACKGROUND OF THE INVENTION

1. Field of the Invention

The present invention relates to an improvement in an ophthalmic instrument equipped with an alignment function which automatically aligns the main body of the instrument with a subject eye to be tested.

2. Description of the Related Art

A conventional ophthalmic instrument with an alignment function, such as a non-contact type tonometer, is provided with a stopper which limits the range in which the main body of the instrument moves in the back-and-forth direction, for the purpose of avoiding a collision between a testee and the main body of the instrument. This stopper can adjust its position as needed and is constructed so that it can change the moving range of the main body of the instrument. And a tester adjusts the minimum distance between the main body of the instrument and a testee by adjusting the position of this stopper.

Incidentally, it has also been proposed that during position adjustment of the stopper, the drive of a measuring portion by an automatic alignment function is limited (Japanese Laid-Open Patent Publication No. HEI 8-266475). That is, if a knob for moving the stopper is pushed, the stopper is moved and the movable range of the main body of the instrument is changed. While this stopper moving knob has been pushed, the drive of a drive portion for driving the measuring portion is inhibited. With this, it can be avoided that unnecessary measurement is performed during the position adjustment of the stopper.

However, the above-mentioned prior art can avoid only unnecessary measurement during the position adjustment of the stopper, but it cannot avoid unnecessary measurement immediately after the tester releases hold of the stopper moving knob. That is, at the time the tester has released hold of the stopper moving knob, there are cases where accidentally the main body of the instrument is at a position which satisfies alignment start conditions. And in such cases, there is a fear that the conventional ophthalmic instrument will start a measurement which the tester does not intend.

SUMMARY OF THE INVENTION

An object of the present invention is to provide an ophthalmic instrument which is capable of avoiding unnecessary measurement which a tester does not intend.

To achieve this end, there is provided an ophthalmic instrument equipped with: an operating stick for performing rough alignment on a main body of the instrument against a subject eye to be tested; alignment detection means for detecting a state of alignment between the main body and the subject eye; and drive means for driving the main body on the basis of a result of detection of the alignment detection means and performing precise alignment on the main body against the subject eye. The ophthalmic instrument comprises: limitation means for limiting a range in which the main body moves; change means for changing the range limited by the limitation means; first detection means for detecting a change operation of the change means; second detection means for detecting that the main body is at a distance away from the subject eye by a predetermined value or greater; inhibition means for inhibiting drive of the drive means when the first detection means detects the change operation of the change means; and allowance means for allowing drive of the drive means, when the first detection means detects an end of the change operation of the change means and also the second detection means detects that the main body is at a distance away from the subject eye by a predetermined value or greater.

In the ophthalmic instrument of the present invention, automatic alignment is not executed only when the change operation of the change means ends. When the change operation of the change means ends and also when it is detected that the main body of the instrument is at a distance away from the subject eye by a predetermined value or greater, drive of the drive means is allowed for the first time and automatic alignment is executed. With this, unnecessary measurement which is not intended by the tester can be avoided.

BRIEF DESCRIPTION OF THE DRAWINGS

The above and other objects and advantages will become apparent from the following detailed description when read in conjunction with the accompanying drawings wherein.

DETAILED DESCRIPTION OF THE PREFERRED EMBODIMENT

A preferred embodiment of this invention will hereinafter be described according to the drawings.

Figure 1:
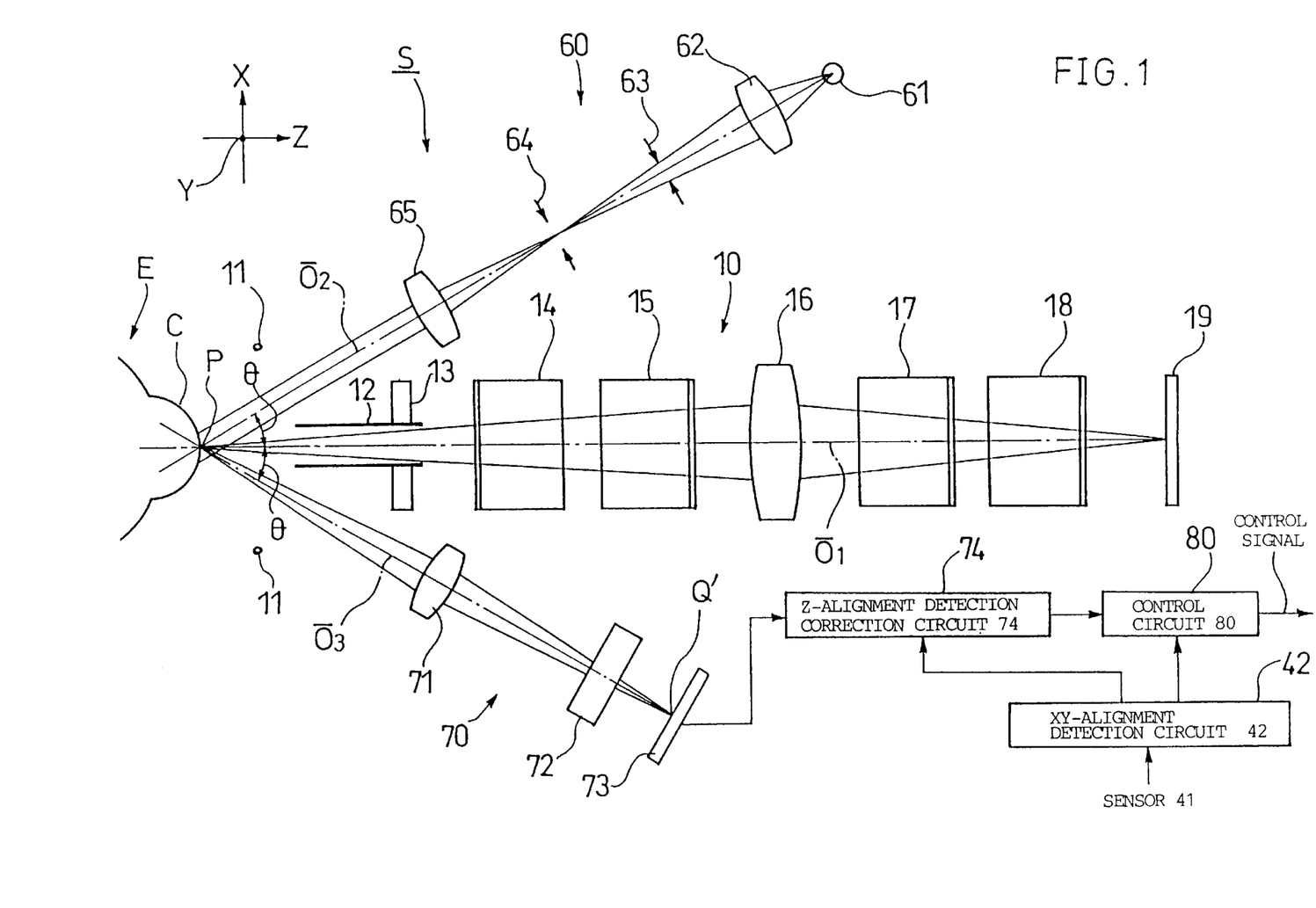
FIG. 1 is a plan view showing the optical system of an ophthalmic instrument according to the present invention.
Figure 2:
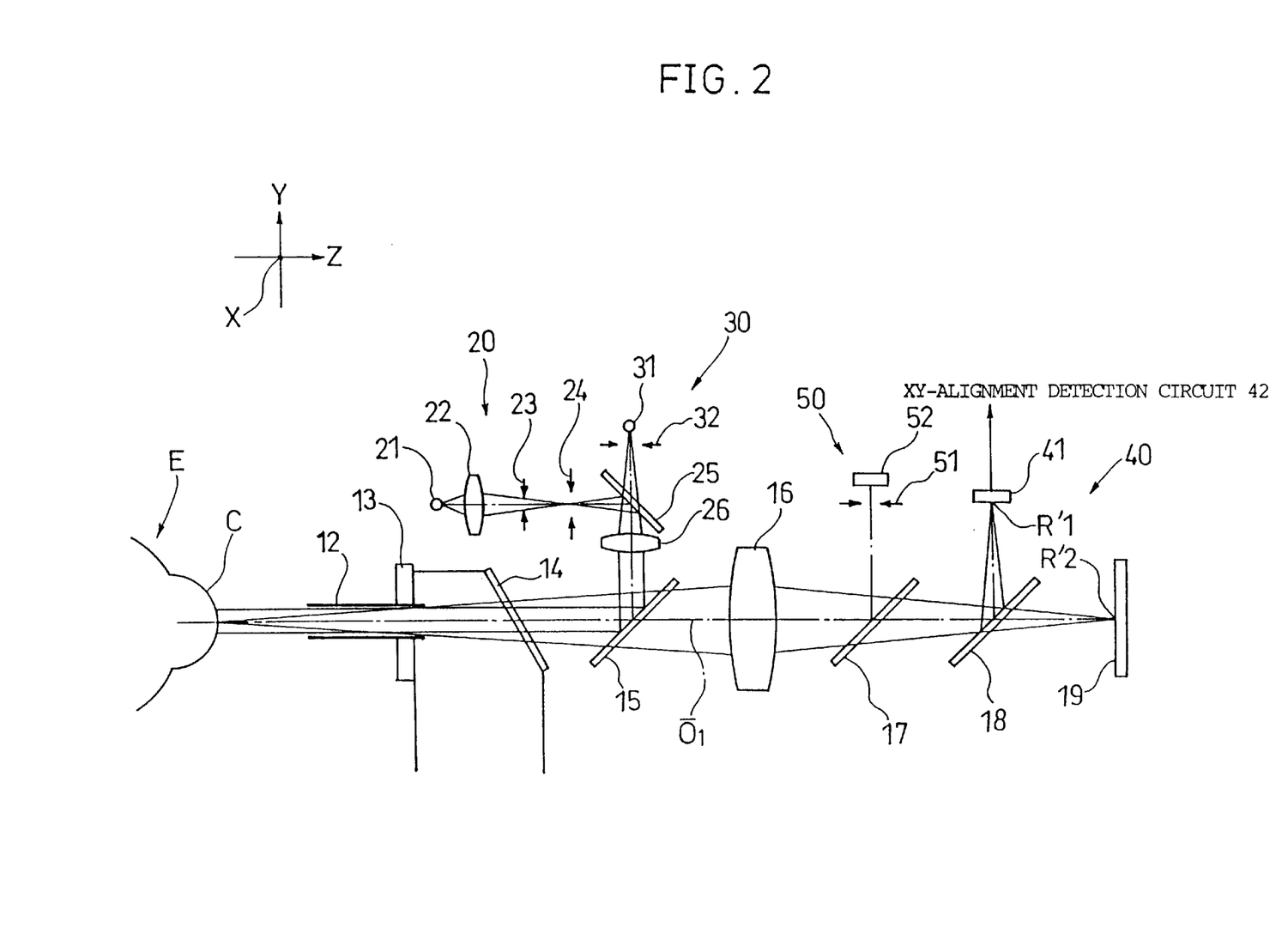
FIG. 2 is a side view showing the optical system of the ophthalmic instrument according to the present invention.

In FIGS. 1 and 2 an ophthalmic instrument S according to the present invention is equipped with a front eye portion observation optical system 10 for observing the front eye portion of a subject eye E, an XY-alignment index projection optical system 20 for projecting index light for alignment detection and cornea deformation detection in X and Y directions onto the cornea C of the subject eye E from the front surface, and a fixed index projection optical system 30 for providing a fixed index to the subject eye E. The ophthalmic instrument S is further equipped with an XY-aligament detection optical system 40 for receiving the reflected light of XY-alignment index light reflected at the cornea C and detecting the positional relation in XY direction between the instrument S and the cornea C, a cornea deformation detection optical system 50 for receiving the reflected light of XY-alignment index light reflected at the cornea C and detecting the deformation quantity of the cornea C, a Z-alignment index projection optical system 60 for projecting Z-alignment index light onto the cornea C from an oblique direction, and a Z-alignment detection optical system 70 for receiving the reflected light of Z-alignment index light reflected at the cornea C from a direction symmetrical with the optical axis of the front eye portion observation optical system 10 and detecting the positional relation in Z direction between the instrument S and the cornea C.

The front eye portion observation optical system 10 is equipped with a plurality of front eye portion illumination light sources 11 located at the right and left of the subject eye E to illuminate the front eye portion directly, an air spraying nozzle 12, a front eye portion window glass 13, a chamber window glass 14, a half mirror 15, an objective lens 16, half mirrors 17 and 18, and a charge coupled device (CCD) camera 19. The optical axis of this system 10 is represented by O1.

The image of the front eye portion of the subject eye E, illuminated by the front eye portion illumination light source 11, passes through the inside and outside of the air spraying nozzle 12 and are transmitted through the front eye portion window glass 13, chamber window glass 14, and half mirror 15. The transmitted image is transmitted through the half mirrors 17 and 18 while being focused by the objective lens 16 and is formed on the CCD camera 19.

The XY-alignment index projection optical system 20 has an XY-alignment light source 21 for emitting infrared light, a condenser lens 22, an aperture diaphragm 23, a pinhole plate 24, a dichroic mirror 25, and a projection lens 26 arranged in an optical path so that its focal point is aligned with the pinhole plate 24. The system 20 further has the aforementioned half mirror 15, chamber window glass 14, and air spraying nozzle 12.

Figure 3:
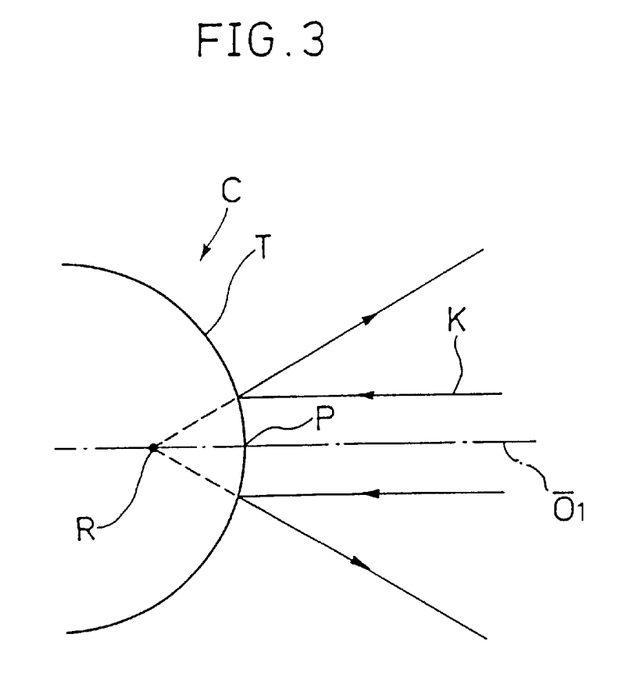
FIG. 3 is an explanatory diagram of the reflection of an alignment beam of light frontally projected onto a cornea.

Infrared light emitted from the XY-alignment light source 21 passes through the aperture diaphragm 23 while being focused by the condenser lens 22, and is guided to the pinhole plate 24. And the beam of light, which has passed through the pinhole plate 24, is reflected by the dichroic mirror 25 and is changed to a collimated beam of light by the projection lens 26. After the collimated light beam has been reflected by the half mirror 15, it is transmitted through the chamber window glass 14 and passes through the inside of the air spraying nozzle 12. Finally, the light beam forms XY-alignment index light K as shown in FIG. 3. In the figure the XY-alignment index light K is reflected at the cornea surface T so that a bright point image R is formed at the intermediate point between the vertex P of the cornea C and the center of curvature of the cornea C. Note that the aperture diaphragm 23 is provided at a position conjugate with the vertex P of the cornea C with respect to the projection lens 26.

The fixed index optical system 30 has a fixed index light source 31 for emitting visible light and a pinhole plate 32. The fixed index optical system 30 further has the aforementioned dichroic mirror 25, projection lens 26, half mirror 15, chamber window glass 14, and air spraying nozzle 12.

Fixed index light emitted from the fixed index light source 31 passes through the pinhole plate 32 and the dichroic mirror 25 and is collimated by the projection lens 26. After the collimated light beam has been reflected by the half mirror 15, it is transmitted through the chamber window glass 14. The transmitted light beam passes through the inside of the air spraying nozzle 12 and is guided to the subject eye E. The testee gazes steadily at the fixed index as a fixed target, whereby a line of sight is locked.

The XY-alignment detection optical system 40 has the aforementioned air spraying nozzle 12, chamber window glass 14, half mirror 15, objective lens 16, and half mirrors 17 and 18. The XY-alignment detection optical system 40 further has a sensor 41 and an XY-alignment detection circuit 42. To intercept extra light, a diaphragm with a sufficiently large opening may be arranged directly before the sensor 41.

The reflected light beam, projected on the cornea C and reflected at the cornea surface T by the XY-alignment index projection optical system 20, passes through the inside of the nozzle 12 and is transmitted through the chamber window glass 14 and the half mirror 15. The transmitted light is partially transmitted through the half mirror 17 while being focused by the objective lens 16, and a portion of the light transmitted through the half mirror 17 is reflected at the half mirror 18. The light beam, reflected at the half mirror 18, forms a bright point image R'1 on the sensor 41. The sensor 41 is a light receiving sensor, such as a PSD, which can detect position. The XY-alignment detection circuit 42 computes the positional relation (XY direction) between the instrument S and the cornea C by a known means on the basis of the output of the sensor 41, and outputs the result of computation to a Z-alignment detection correction circuit 74 and a control circuit 80.

Figure 4:
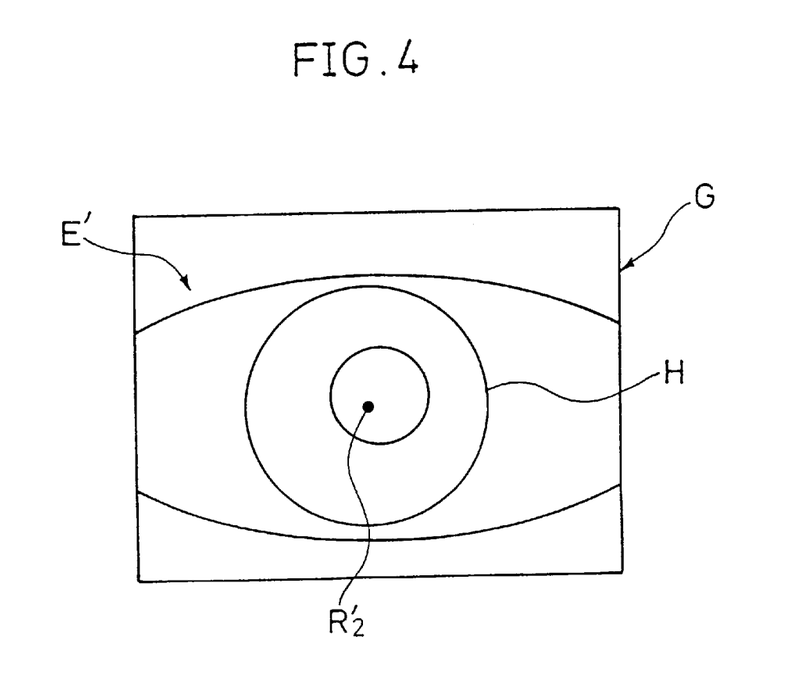
FIG. 4 is a diagram showing the image of the front eye portion displayed on the screen of a monitor.

On the other hand, the light beam, reflected at the cornea C and transmitted through the half mirror 18, forms a bright point image R'2 on the CCD camera 19. The CCD camera 19 outputs an image signal to a monitor, and as shown in FIG. 4, the front eye portion image E' of the subject eye E and the bright point image R'2 of the XY-alignment index light are displayed on the screen G of the monitor. In FIG. 4, reference character H denotes an alignment auxiliary mark produced by image producing means (not shown).

Furthermore, the partial light beam reflected by the half mirror 17 is guided to the cornea deformation detection optical system 50. The light beam passes through a pinhole plate 51 and is guided to a sensor 52. The sensor 52 is a light receiving sensor, such as a photodiode, which can detect a quantity of light.

The Z-alignment index projection optical system 60 has a Z-alignment light source 61 for emitting infrared light, a condenser lens 62, an aperture diaphragm 63, a pinhole plate 64, and a projection lens 65 arranged in an optical path so that its focal point is aligned with the pinhole plate 64. The optical axis of this system 60 is represented by O2.

Figure 5:
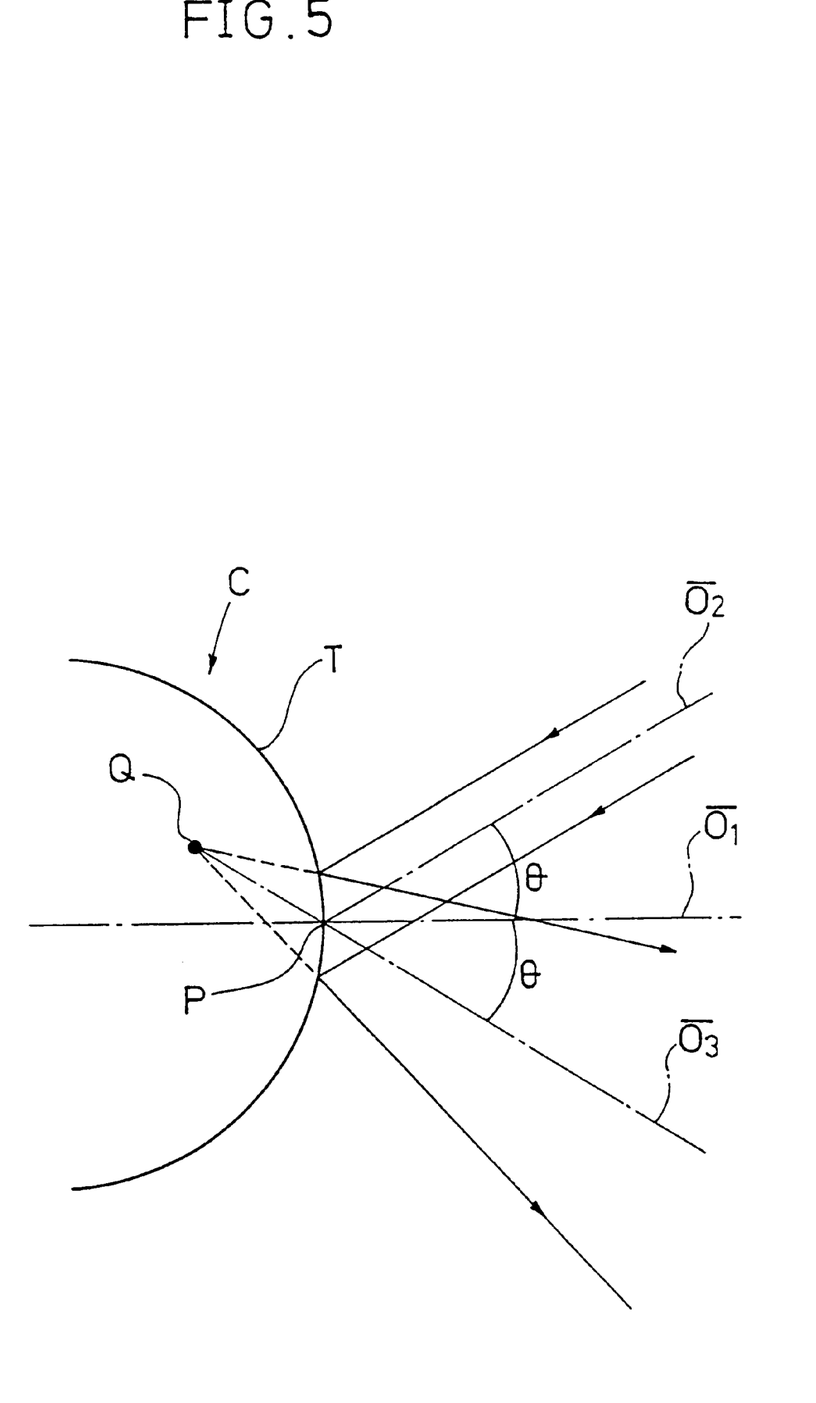
FIG. 5 is an explanatory diagram of the reflection of an alignment beam of light projected onto the cornea from an oblique direction.

Infrared light emitted from the Z-alignment light source 61 passes through the aperture diaphragm 63 while being focused by the condenser lens 62, and is guided to the pinhole plate 64. The light beam transmitted through the pinhole plate 64 is collimated by the projection lens 65 and is guided to the cornea C. As shown in FIG. 5, the light beam is reflected at the cornea surface T so that it forms a bright point image Q. Note that the aperture diaphragm 63 is provided at a position conjugate with the vertex P of the cornea C with respect to the projection lens 65.

The Z-alignment detection optical system 70 has an image forming lens 71, a cylindrical lens 72 having power in a Y direction, a sensor 73, and a Z-alignment detection correction circuit 74. The optical axis of this system 70 is represented by O3.

The reflected light at the cornea surface T of the index light projected by the Z-alignment index projection optical system 60 forms a bright point image Q' on the sensor 73 through the cylindrical lens 72 while being focused by the image forming lens 71. The sensor 73 is a light receiving sensor, such as a line sensor or a PSD, which can detect position. Information from the sensor 73 is guided to the Z-alignment detection correction circuit 74 and furthermore it is transmitted to the control circuit 80 (FIG. 1).

On the XZ plane, the bright point image Q and the sensor 73 are in a relation of conjugate position with respect to the image forming lens 71. On the YZ plane, the vertex P of the cornea and the sensor 73 are in a relation of conjugate position with respect to the image forming lens 71 and cylindrical lens 72. In other words, the sensor 73 and the aperture diaphragm 63 are in a conjugate relation (the magnification at this time is selected so that the image of the aperture diaphragm 63 is less than the size of the sensor 73). Therefore, even if the cornea C were shifted in the Y direction, the reflected light at the cornea surface T will be efficiently incident on the sensor 73. Also, if long-slit light is projected in the Y direction, the efficiency will be reduced, but the same effect can be obtained.

Incidentally, in the aforementioned embodiment, as shown in FIG. 1, the projection system and light receiving system for alignment in the Z direction are the Z-alignment index projection optical system 60 and the Z-alignment detection optical system 70, and they are provided one by one respectively. In constitution such as this, in order to perform alignment in the Z direction accurately without the influence of an alignment shift in the XY direction, the XY-alignment information from the XY-alignment detection circuit 42 is input to the Z-alignment detection correction circuit 74.

Figure 6A:
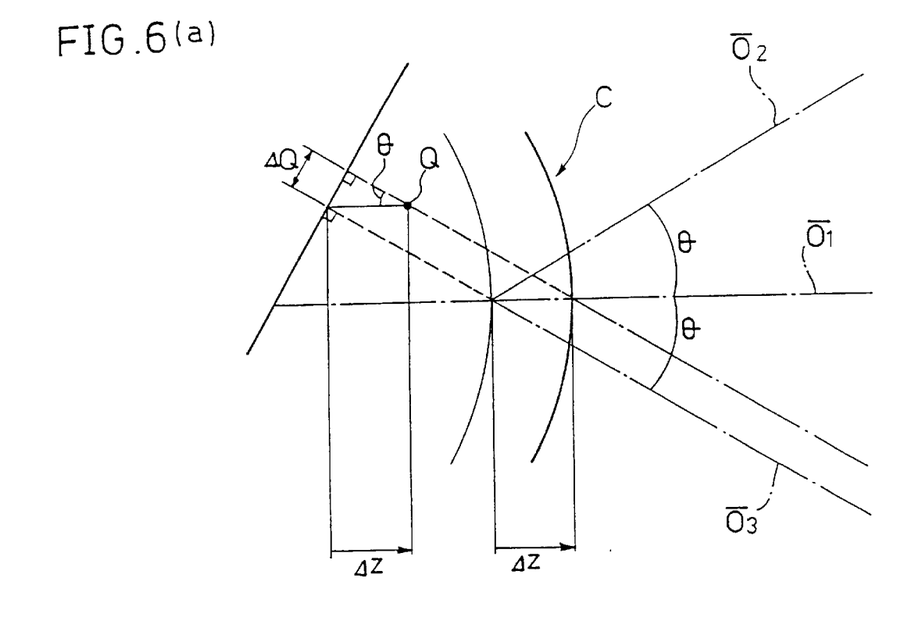
FIG. 6(a) an explanatory diagram showing the relation of incident light and reflected light in the case where the position of a cornea was shifted, the cornea having been shifted in a Z direction.

That is, as shown in FIG. 6(a), in the case where the position of the cornea C is shifted $\Delta Z$ in the Z direction, the position of the bright point image Q' is moved on the sensor 73 by $\Delta Z \times \sin \theta \times m$. Herein, $\theta$ is the angle between the axis O1 and the axis O2 or between the axis O1 and the axis O3, and m is the image forming magnification of the Z-alignment optical system 70. If the cornea C is shifted only in the Z direction, the shift quantity of the cornea C can be easily computed from the quantity of movement of the bright point image Q' on the sensor 73.

Figure 6B:
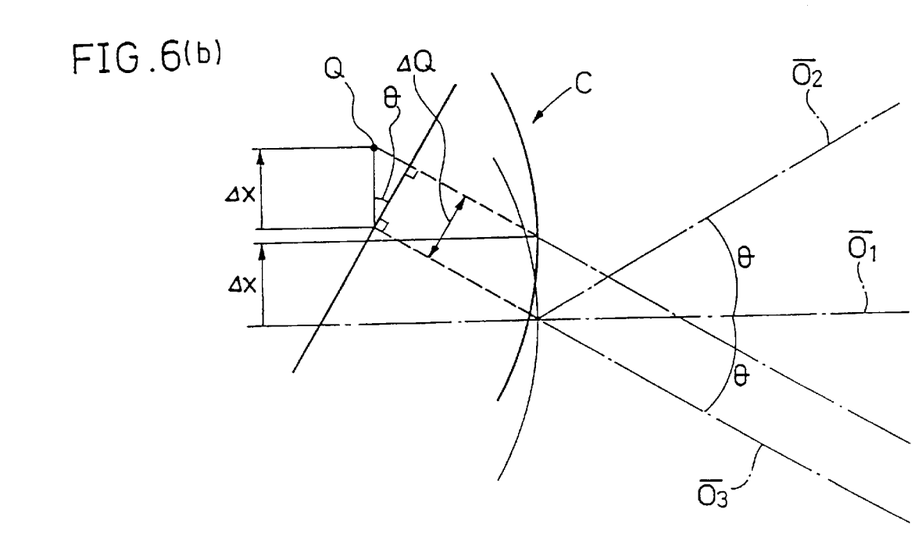
FIG. 6(b) an explanatory diagram showing the relation of incident light and reflected light in the case where the position of a cornea was shifted, the cornea having been shifted in an X direction.

However, as shown in FIG. 6(b), even in the case where the position of the cornea C is shifted $\Delta X$ in the X direction, the position of the bright point image Q' is moved on the sensor 73 by $\Delta X \times \cos \theta \times m$. Hence, in the case where the position of the cornea C is shifted in both the Z direction and the Y direction, the Z-alignment detection correction circuit 74 computes the positional relation in Z-direction between the instrument S and the cornea C (i.e., shift quantity $\Delta Z$) from the shift quantity $\Delta Q'$ of the bright point image Q' from a reference position on the sensor 73 and also from the shift quantity $\Delta X$ from the XY-alignment detection circuit 42, based on the following equation (1), and outputs the result of computation to the control circuit 80.

$$\Delta Z = (\Delta Q' - \Delta X \times \cos \theta \times m)/(\sin \theta \times m) \quad (1)$$

Figure 7:
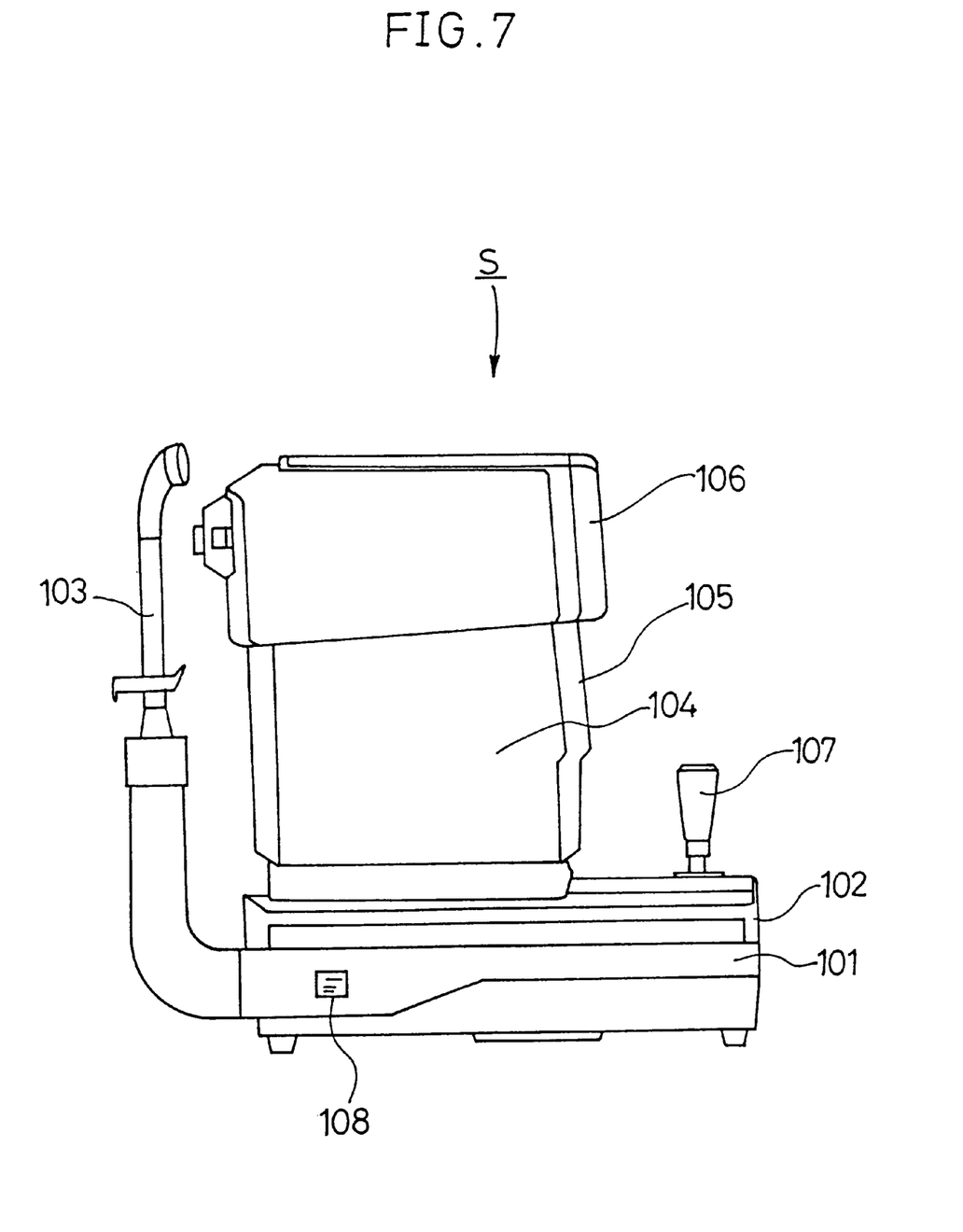
FIG. 7 is an exterior appearance view of the ophthalmic instrument according to the present invention.

FIG. 7 shows an exterior appearance diagram of the ophthalmic instrument S according to the present invention. In the figure, a platform portion 102 is placed on a base 101, and a power supply (not shown) is provided interiorly of the base 101. Also, to the base 101 a chin receiver 103 is attached for locking the face of a testee. A main body portion 104 is provided on the platform portion 102, and a monitor 105 is fixed on this main body portion 104 for displaying a subject eye, measured data, measured indexes, etc. A measuring portion 106 is provided on the main body portion 104. Also, a joy stick 107 (also called an operating stick) is attached to the platform portion 102. If this joy stick 107 is operated, the main body portion 104, monitor 105, and measuring portion 106 are moved with the platform portion 102 in a back-and-forth direction and a right-and-left direction, whereby the measuring portion 106 can be roughly aligned with respect to a subject eye. The back-and-forth direction refers to the right-and-left direction of FIG. 7 (i.e., the Z direction in FIGS. 1 and 2), while the right-and-left direction refers to the direction perpendicular to the paper surface of FIG. 7 (i.e., the X direction in FIGS. 1 and 2).

Figure 11:
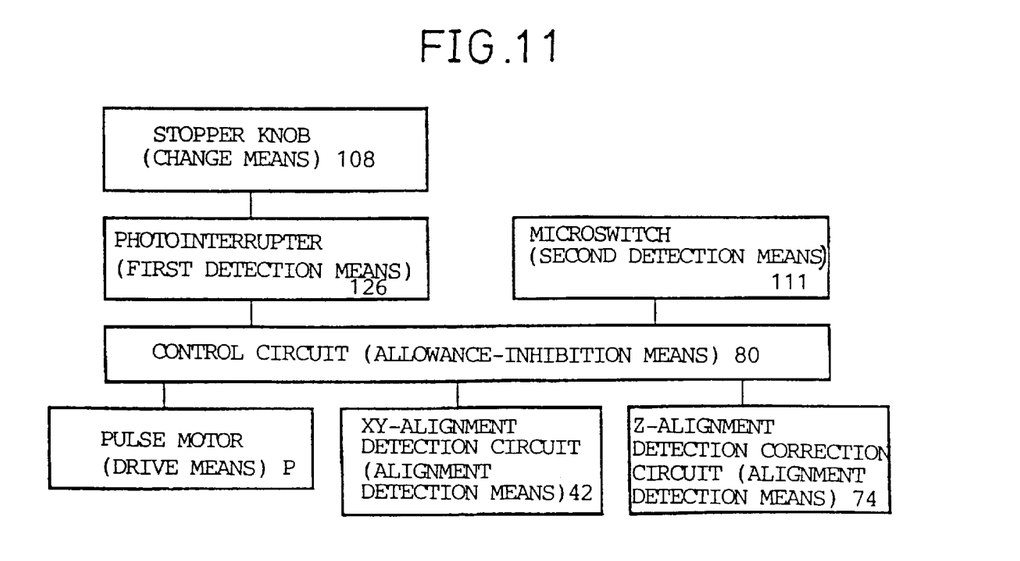
FIG. 11 is a block diagram of the ophthalmic instrument according to the present invention.

A stopper knob 108 is attached to the side surface of the base 101. If this stopper knob 108 is operated, the range in which the platform portion 102, etc., are moved by the joy stick 107 can be changed. Also, the joy stick 107 is provided with a switch (not shown) for detecting its rotation. When the joy stick 107 is rotated, the aforementioned switch is turned on and a pulse motor P (not shown) for driving the measuring portion 106 in an up-and-down direction (Y direction) is driven. If the aforementioned rough alignment by the joy stick 107 ends, the control circuit 80 will output a pulse signal corresponding to the outputs of the X-alignment detection circuit 42 and z-alignment detection correction circuit 74 toward the pulse motor P for driving the measuring portion 106 in X,Y, and Z directions (FIG. 11). With this, the accurate and final alignment of the measuring portion 106 against a subject eye is achieved.

Figure 8:
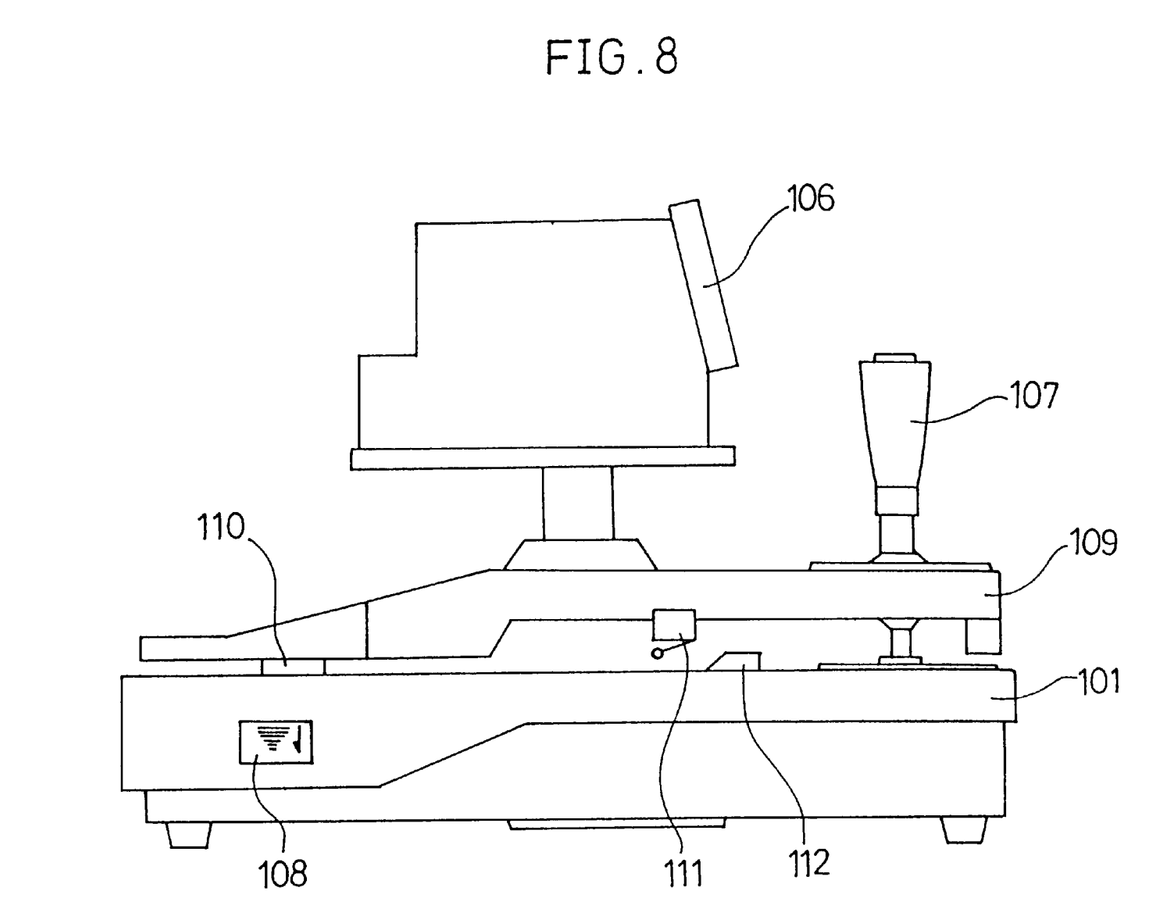
FIG. 8 is a side view showing the interior constitution of a main body portion provided on a base.

FIG. 8 illustrates the measuring portion 106 with the main body portion 104 and the cover of the platform portion 102 removed. As shown in FIG. 8, a platform frame 109 forming the framework of the platform portion 102 is provided on the base 101. The tester's side (right side of FIG. 8) of this platform frame 109 is supported on the base 101 through the joy stick 107, while the testee's side (left side of FIG. 8) is supported on the base 101 through a boss 110. The boss 110 is connected to a retainer within the base 101. The retainer will be described later.

Also, a microswitch 111 is attached to a predetermined place on the platform frame 109. This microswitch 111 is engageable with a protruding portion 112 provided on the base 101. If the platform frame 109 is moved to the tester's side, the microswitch 111 will engage with the protruding portion 112 and be turned on. In addition, the output of this microswitch 111 is transmitted to the control circuit 80 (FIG. 11).

Figure 9:
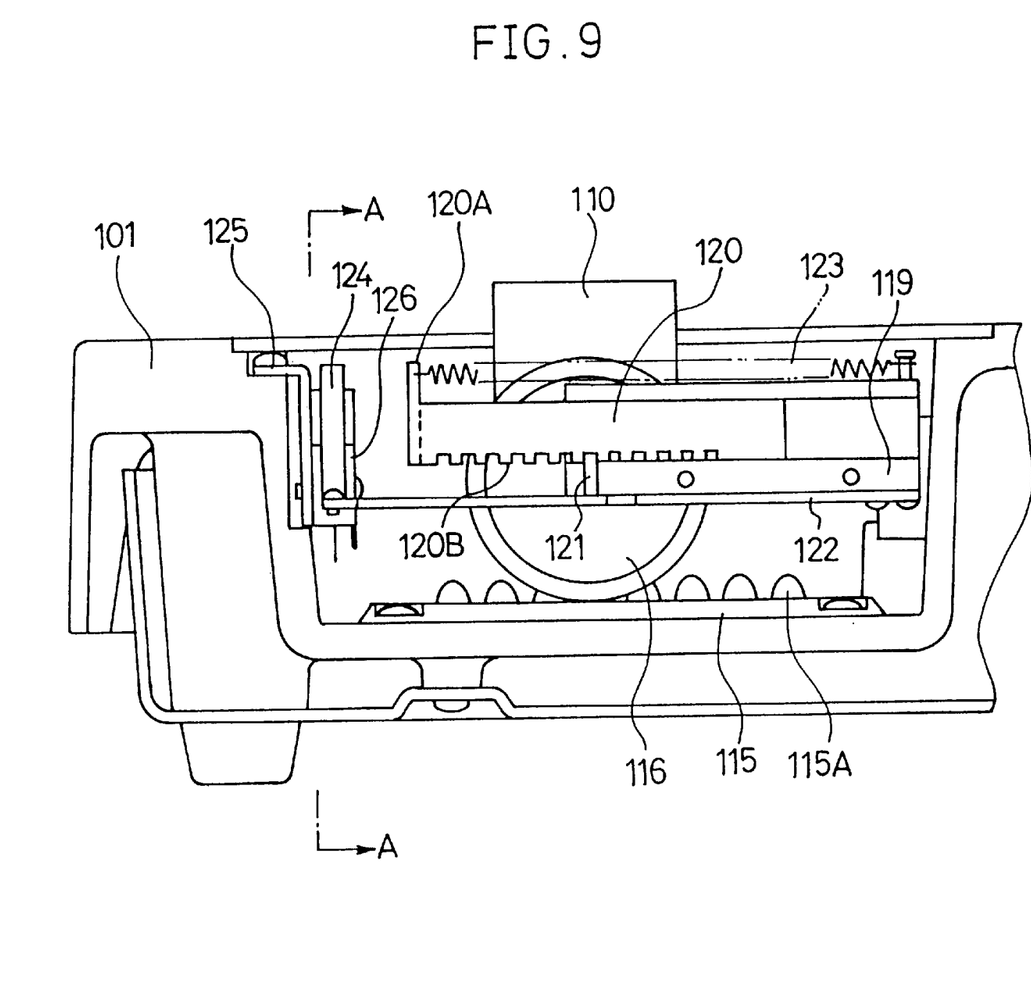
FIG. 9 is an enlarged view showing the vicinity of the stopper knob of the interior constitution of the base.
Figure 10:
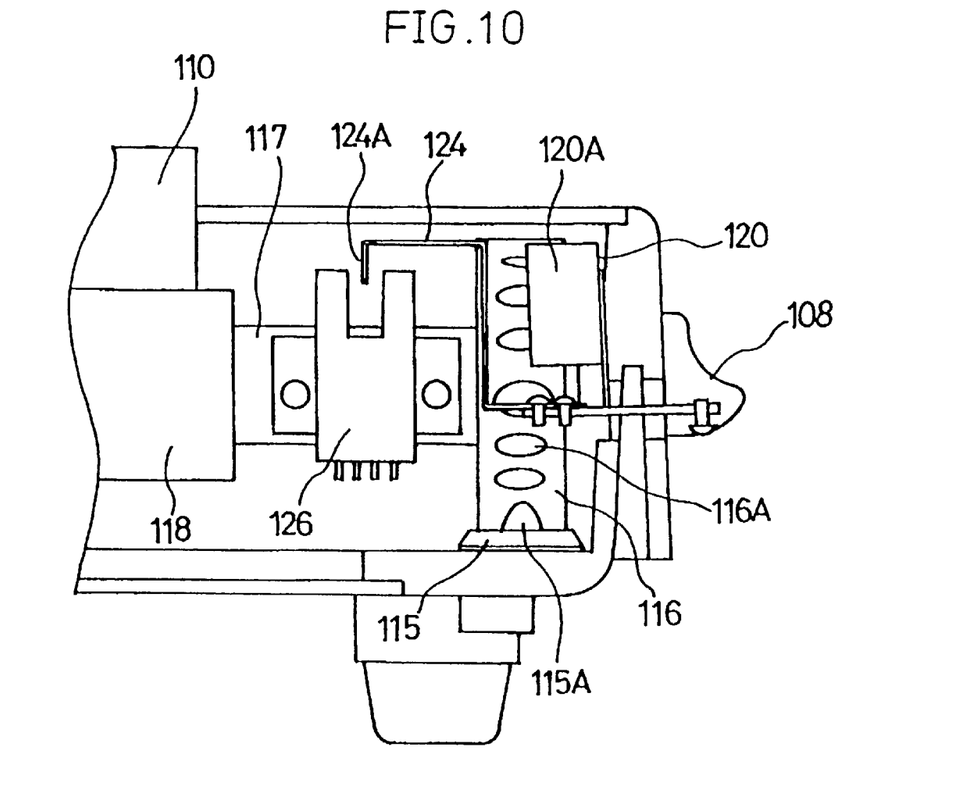
FIG. 10 is a sectional view taken along the line A—A of FIG. 9.

FIG. 9 shows the inner construction of the base 101 and is an enlarged view of the vicinity of the stopper knob 108. FIG. 10 is a sectional view along the line A—A of FIG. 9. In the interior of the base 101 a rail 111 is fixed in the back-and-forth direction of the base 101. On this rail 115 a wheel 116 is installed. The rail 115 is provided with protrusions 115A at constant intervals. The wheel 116 is formed with holes 116A in its outer circumferential surface as shown in FIG. 10. When the wheel 116 rotates on the rail 115, the protrusion 115A is fitted into the hole 116A.

In FIG. 10, although only the wheel on one side is shown, another wheel is provided on the opposite side. The two wheels are interconnected by an axle shaft 117. The axle shaft 117 is inserted into the retainer 118 to which the boss 110 is connected. Although not shown, a plurality of bearing balls are provided interiorly of the retainer 118. The retainer 118 is freely slidable along the axle shaft 117.

As described above, the wheels 116 are freely rotatable along the rails 115 and also the retainer 118 is freely slidable along the axle shaft 117, so the boss 110 connected to the retainer 118 is freely movable in the back-and-forth direction and the right-and-left direction. With this, the platform frame 109 supported by the boss 110 is also freely movable in the back-and-forth direction and right-and-left direction. Also, as shown in FIG. 9, a stopper holder 119 is fixed to the base 101 in parallel to the rail 115. Within the stopper holder 119 a stopper 120 is provided freely slidable. The stopper 120 is bent at its point end (left side of FIG. 9) toward the side of the wheel 116, and the bent portion 120A can contact with the exterior circumferential surface of the wheel 116. Also, the lower portion of the stopper 120 is formed with a plurality of comb-shaped recesses 120B in which a pin 121 is fitted.

A plate spring 122 is fixed to the lower portion of the stopper holder 120, and the aforementioned pin 121 is attached to the central portion of the plate spring 122. The point end of the plate spring 122 is coupled to the stopper knob 108 as shown in FIG. 10. If the stopper knob 108 is operated up and down, the point end of the plate spring 122 will be moved up and down, and at the same time, the pin 121 will also be moved up and down. With this, the pin 121 can be fitted into the recess 120B of the stopper 120, or it can be pulled out from the recess 120B.

Also, the upper portion of the stopper holder 119 is coupled to one end of a coil spring 123, and the other end of the coil spring 123 is coupled to the bent portion 120A of the stopper 120. The coil spring 120 is a tension spring, which urges the stopper 120 in a pull-back direction (i.e., right direction of FIG. 9).

A light intercepting plate 124 is attached to the point end of the plate spring 124. This light intercepting plate 124 is bent into an L shape, and furthermore, the point end is bent downward. The bent portion 124A of the point end can be moved into or out from between the light emitting portion and light receiving portion of a photointerrutper 126 fixed to the base 101 through a bracket 125. If the stopper knob 108 is moved downward, the point end of the plate spring 122 will move down, and at the same time, the bent portion 124A of the point end of the light intercepting plate 124 will be moved into between the light emitting portion and light receiving portion of the photointerrupter 126 and interrupt the photointerrupter 126 Also, if the stopper knob 108 is moved upward, the point end of the plate spring 122 will rise by the urging force of the plate spring 122 itself, and at the same time, the bent portion 124A of the point end of the light intercepting plate 124 will be moved out from between the light emitting portion and light receiving portion of the photointerrupter 126, so that the interruption of the photointerrupter 126 by the plate 124 is released. The output of the photointerrupter 126 is transmitted to the control circuit 80 (FIG. 11).

Now, the operation of the ophthalmic instrument S of the aforementioned constitution will be described.

First, a testee places the chin on the chin receiver 103, and a tester lowers the stopper knob 108. If done in this way, as previously described, the light intercepting plate 124 will fall at the same time and the bent portion 124A of the point end of the plate 124 will interrupt the photointerrupter 126. With this operation, it is detected that the stopper knob 108 has been operated. Based on this detection signal the control circuit 80 stops the transmission of the pulse signal to the pulse motor P. That is, driving the measuring portion 106 is inhibited.

Also, if the stopper knob 108 is lowered, the pin 121 will be pulled out from the recess 120B of the stopper 120 and the stopper 120 will be pulled back to the tester's side, so that the bent portion 120A will be brought into contact with the exterior circumferential surfaces of the wheels 116. With this state, the tester operates the joy stick 107 and advances the platform portion 102. When the distance between the cornea of the testee and the measuring portion 106 is slightly shorter than the operating distance, the tester releases the stopper knob 108.

If the stopper knob 108 is released, the plate spring 122 will jump by the restoring force thereof and return to its original position. Therefore, the light intercepting plate 124 rises and the bent portion 124A of the point end of the plate 124 is moved out from between the light emitting portion and the light receiving portion of the photointerrupter 126, so that the interruption of the photointerrupter 126 by the plate 124 is released. With this, the control circuit 80 detects that the stopper knob 108 has not been operated. However, with only this, the release of the drive stop of the measuring portion 106 is not performed.

Also, at the same time the stopper knob 108 is released, the pin 121 is fitted into any one of the comb-shaped recesses 120B formed in the lower portion of the stopper 120 and stops the stopper 120, so that the advancement of the platform portion 102 is interrupted at that position. Note that it is a matter of course that a sufficiently greater distance than the quantity by which the measuring portion 106 can automatically advance should be present between the measuring portion 106 and the cornea of the testee.

Next, if the tester pulls on this side the joy stick 107 and moves the platform portion 102 to the tester's side, the microswitch 111 will engage with the protruding portion 112 of the base 101 and be turned on. At this stage, the control circuit 80 releases the drive stop of the measuring portion 106 for the first time.

And next, the tester moves the platform portion 102 by moving the joy stick 107 in the back-and-forth direction and right-and-left direction, thereby adjusting the position of the measuring portion 106 in the X and Z directions. At the same time, the tester moves the measuring portion 106 in the up-and-down direction by rotating the joy stick 107, thereby adjusting the position of the measuring portion 106 in the Y direction.

If the rough alignment has been completed and the measuring portion 106 is set against the cornea in a predetermined wide range, the control circuit 80 will transmit a control circuit on the basis of the information from the XY-alignment detection circuit 42 and Z-alignment detection correction circuit 74 and control the pulse motors P for X direction, Y direction, and Z direction of the measuring-portion drive unit (not shown), thereby moving the measuring portion 106 automatically in the X, Y, and Z directions and moving the measuring portion 106 into a predetermined narrow range against the cornea. With this, if the alignment between the instrument S and the cornea is completed, air will be injected onto the cornea of the subject eye through the nozzle from the air injector, and the intraocular pressure of the subject eye is computed by a known technique from the pressure of the air injector when the cornea is deformed into a predetermined shape.

According to the embodiment of the present invention, the drive of the measuring portion 106 is in a stopped state until the microswitch 111 engages with the protruding portion 112 of the base 101. Therefore, since automatic alignment is not executed only when the tester releases hold of the stopper knob 108, the aforementioned unnecessary measurement can be avoided.

While the present invention has been fully described with relation to the preferred embodiment thereof, the invention is not to be limited to the details given herein, but may be modified within the scope of the appended claims.

What is claimed is:

1. An ophthalmic instrument equipped with an operating stick for performing rough alignment on a main body of the instrument against an eye to be tested, alignment detection means for detecting a state of alignment between said main body and said eye, and drive means for driving said main body on the basis of a result of detection of said alignment detection means and performing precise alignment on said main body against said eye, the ophthalmic instrument comprising:

limitation means for limiting a range in which said main body moves;

change means for changing the range limited by said limitation means;

first detection means for detecting a change operation of said change means;

second detection means for detecting that said main body is at a distance away from said eye by a predetermined value or greater;

inhibition means for inhibiting drive of said drive means when said first detection means detects the change operation of said change means; and allowance means for allowing drive of said drive means, when said first detection means detects an end of the change operation of said change means and also said second detection means detects that said main body is at a distance away from said eye by a predetermined value or greater.

2. The ophthalmic instrument as set forth in claim 1, wherein said first detection means has a light intercepting plate which moves in interlock with the change operation of said change means, and a photointerrupter which detects that said light intercepting plate shuts out light.

3. The ophthalmic instrument as set forth in claim 1, wherein said second detection means is a microswitch which is provided on said main body or provided on a platform frame placed on said main body so that it is freely movable.

* * * * *